US009091770B2

(12) United States Patent
Okada

(10) Patent No.: US 9,091,770 B2
(45) Date of Patent: Jul. 28, 2015

(54) RADIATION DETECTOR, RADIOGRAPHIC IMAGING DEVICE, AND RADIOGRAPHIC IMAGING SYSTEM

(71) Applicant: FUJIFILM Corporation, Tokyo (JP)

(72) Inventor: Yoshihiro Okada, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 325 days.

(21) Appl. No.: 13/688,047

(22) Filed: Nov. 28, 2012

(65) Prior Publication Data
US 2013/0136233 A1 May 30, 2013

(30) Foreign Application Priority Data
Nov. 30, 2011 (JP) ................. 2011-263016

(51) Int. Cl.
*H01L 27/146* (2006.01)
*G01T 1/24* (2006.01)
*G01N 23/04* (2006.01)
(Continued)

(52) U.S. Cl.
CPC .............. *G01T 1/247* (2013.01); *G01N 23/04* (2013.01); *H01L 27/14663* (2013.01); *H04N 5/32* (2013.01); *H04N 5/378* (2013.01)

(58) Field of Classification Search
CPC ............ H01L 27/146; H01L 27/14601; H01L 27/14603; H01L 27/14609; H01L 27/14658; H01L 27/14676; G01T 1/24; G01T 1/241; G01T 1/247
USPC ................... 378/96, 97, 98.7, 98.8; 250/370.07–370.11, 370.14, 371
See application file for complete search history.

(56) References Cited

U.S. PATENT DOCUMENTS

| 6,535,576 B2* | 3/2003 | Vafi et al. ............ 378/98.8 |
| 7,995,113 B2* | 8/2011 | Karim et al. .......... 348/230.1 |
| 2003/0213914 A1 | 11/2003 | Kobayashi et al. |

(Continued)

FOREIGN PATENT DOCUMENTS

| JP | 2002-300589 A | 10/2002 |
| JP | 2004-130058 A | 4/2004 |

(Continued)

OTHER PUBLICATIONS

Japanese Office Action, dated Nov. 5, 2013, for Japanese Application No. 2011-263016 with an English translation.

*Primary Examiner* — Thomas R Artman
(74) *Attorney, Agent, or Firm* — Birch, Stewart, Kolasch & Birch, LLP

(57) ABSTRACT

The present invention provides radiation detector, radiographic imaging device and radiographic imaging system that may detect irradiated radiation while maintaining quality of radiographic image. The radiation detector has: pixels having a sensor portion that generates charges in accordance with light converted from irradiated radiation, TFT switch that outputs, to a signal line, charges read-out from the sensor portion, and radiation detection TFT switch that is not connected to a signal line; and radiation detection pixels that have the sensor portion, the TFT switch, and radiation detection TFT switch that is connected to a signal line and that outputs, to the signal line, charges read-out from the sensor portion. The radiation detection TFT switches are connected to radiation detection scan lines, and ON/OFF states are controlled by scan signals that are outputted from a radiation detection control circuit.

18 Claims, 14 Drawing Sheets

(51) Int. Cl.
*H04N 5/32* (2006.01)
*H04N 5/378* (2011.01)

(56) References Cited

U.S. PATENT DOCUMENTS

| | | |
|---|---|---|
| 2006/0181628 A1 | 8/2006 | Kish |
| 2007/0187609 A1 | 8/2007 | Karim |
| 2008/0259182 A1* | 10/2008 | Karim et al. ............... 348/230.1 |
| 2011/0180717 A1* | 7/2011 | Okada ...................... 250/370.08 |
| 2013/0136233 A1* | 5/2013 | Okada ............................ 378/62 |

FOREIGN PATENT DOCUMENTS

| | | |
|---|---|---|
| JP | 2004-170216 A | 6/2004 |
| JP | 2006-229362 A | 8/2006 |
| JP | 2006-332219 A | 12/2006 |
| JP | 2007-502061 A | 2/2007 |
| JP | 2008-48458 A | 2/2008 |
| JP | 2009-194633 A | 8/2009 |
| JP | 2011-174908 A | 9/2011 |

* cited by examiner

RADIATION DETECTOR, RADIOGRAPHIC IMAGING DEVICE, AND RADIOGRAPHIC IMAGING SYSTEM

CROSS-REFERENCE TO RELATED APPLICATION

This application claims priority under 35 USC 119 from Japanese Patent Application No. 2011-263016, filed on Nov. 30, 2011, the disclosure of which is incorporated by reference herein.

BACKGROUND OF THE INVENTION

1. Field of the Invention

The present invention relates to a radiation detector, a radiographic imaging device, and a radiographic imaging system. In particular, the present invention relates to a radiation detector, a radiographic imaging device, and a radiographic imaging system for imaging radiographic images.

2. Description of the Related Art

There are conventionally known radiation detectors that are used in radiographic imaging devices for imaging radiographic images for the purpose of medical diagnosis, or the like. The radiation detector detects radiation, that has been irradiated from a radiation irradiating device and has passed through a subject, and captures a radiographic image. The radiation detector carries out imaging of a radiographic image by collecting and reading-out charges that are generated in accordance with the irradiated radiation.

A radiation detector that is formed from plural pixels that each have a sensor portion, that is formed by a photoelectric conversion element or the like and that generates charges due to the irradiation of radiation or of light converted from radiation, and a switching element, that reads-out the charges generated at the sensor portion, is known as such a radiation detector.

There is known a technique of providing, at this radiation detector, radiation detection pixels that have a short-circuited switching element, in order to carry out detection according to the irradiation of radiation, such as the start of irradiation of radiation or the like (see, for example, Japanese Patent Application Laid-Open (JP-A) No. 2011-174908).

In such a technique, at the radiation detection pixels, the switching elements are short-circuited. Therefore, charges are read-out regardless of the states of control (the on/off states) of these switching elements. For example, an electric signal (charge amount), that corresponds to the charge read-out by the short-circuited switching element from a radiation detection pixel, and a predetermined threshold value, are compared, and if the threshold value is exceeded, it is determined that the irradiation of radiation has started.

As in the technique disclosed in JP-A No. 2011-174908, when carrying out detection according to the irradiation of radiation on the basis of electric signals read-out from radiation detection pixels, the difference in the wiring capacities is extremely large at signal lines (hereinafter called "detection lines") through which electric signals read-out from radiation detection pixels flow (i.e., signal lines to which radiation detection pixels are connected), and at signal lines (hereinafter called "regular lines") through which electric signals read-out from regular pixels flow (i.e., signal lines to which radiation detection pixels are not connected, and through which electric signals read-out from radiation detection pixels do not flow). When carrying out imaging of a radiographic image, there are cases in which the output signals of detection lines, to which radiation detection pixels are connected, deteriorate, and a large difference arises between these output signals and the output signals of regular lines.

When a large difference arises between the output signals of detection lines and the output signals of regular lines, the image quality of the captured radiographic image may deteriorate.

In regard thereto, in order to maintain the level of image quality of the radiographic image, the detection lines are treated as defective lines, and image correction is carried out on the basis of information of the surrounding normal pixels (regular pixels). However, in the image correction of line defects, in a unique pattern, correction artifacts are generated, and may become difficult to maintain the level of image quality of the radiographic image.

SUMMARY OF THE INVENTION

The present invention provides a radiation detector, a radiographic imaging device, and a radiographic imaging system that may carry out detection according to the irradiation of radiation while maintaining the quality of a radiographic image.

A first aspect of the present invention is a radiation detector including: plural first pixels including, a first sensor portion that generates charges in accordance with irradiated radiation, and a first switching element that reads-out the charges generated at the first sensor portion and outputs the charges to a signal line; plural second pixels including, a second sensor portion that generates charges in accordance with irradiated radiation, a second switching element that reads-out the charges generated at the second sensor portion and outputs the charges to a signal line, and a radiation detection switching element that reads-out the charges generated at the second sensor portion and outputs the charges to a signal line; plural scan lines that are formed from at least one of a scan line group formed from scan lines to which control terminals of the first switching elements are connected and through which control signals that switch the first switching elements flow, and scan lines to which control terminals of the second switching elements are connected and through which control signals that switch the second switching elements flow, or a scan line group to which the control terminals of the first switching elements and the control terminals of the second switching elements are connected and through which control signals that switch the first switching elements and the second switching elements flow; and plural radiation detection scan lines that are provided between predetermined scan lines among the plurality of scan lines, and to which control terminals of the radiation detection switching elements are connected, and through which radiation detection control signals that switch the radiation detection switching elements flow.

In a second aspect of the present invention, in the above first aspect, each of the first pixels may include the radiation detection switching element whose a control terminal is connected to the radiation detection scan line and that is not connected to a signal line.

In a third aspect of the present invention, in the above aspects, the first pixels and the second pixels may be configured to have shapes that are line-symmetrical across the radiation detection scan lines.

In a fourth aspect of the present invention, in the above aspects, the plural radiation detection scan lines may be connected, per each predetermined number thereof, to a radiation detection control circuit from which the radiation detection control signals are outputted.

A fifth aspect of the present invention is a radiographic imaging device including: the radiation detector of the above aspects; a radiation detection control circuit that outputs the radiation detection control signals to the radiation detection switching elements of the radiation detector; and detecting section for carrying out predetermined detection according to irradiation of radiation, on the basis of electric signals corresponding to charges that are outputted to the signal lines from the radiation detection witching elements of the second pixels.

In a sixth aspect of the present invention, in the above fifth aspect, during a detection period in which a start of irradiation of radiation is detected by the detecting section, control signals that set the first switching elements and the second switching elements in OFF states may flow to the scan lines, and the radiation detection control signals that set the radiation detection switching elements in ON states may flow to the radiation detection scan lines.

In a seventh aspect of the present invention, in the above fifth and sixth aspects, during the detection period, a resetting operation, that resets charges accumulated in the first pixels and the second pixels may be repeated at a predetermined cycle, by flowing control signals that set the first switching elements and the second switching elements in ON states to the scan lines.

In an eighth aspect of the present invention, in the above fifth through seventh aspects, when the first switching elements and the second switching elements are set in ON states and the charges for radiographic image imaging are outputted from the first pixels and the second pixels to the signal lines, the radiation detection switching elements may be set in OFF states.

A ninth aspect of the present invention is a radiographic imaging system including: an irradiation device that irradiates radiation; and the radiographic imaging device of any one of the fifth through eight aspects that detects radiation irradiated from the irradiation device and acquires a radiographic image corresponding to detected radiation.

In accordance with the above aspects, present invention may provide a radiation detector, a radiographic imaging device, and a radiographic imaging system that may carry out detection according to the irradiation of radiation while maintaining the quality of a radiographic image.

BRIEF DESCRIPTION OF THE DRAWINGS

Exemplary embodiments of the present invention will be described in detail based on the following figures, wherein.

DETAILED DESCRIPTION OF THE INVENTION

An example of a present exemplary embodiment is described hereinafter with reference to the drawings.

Figure 1:
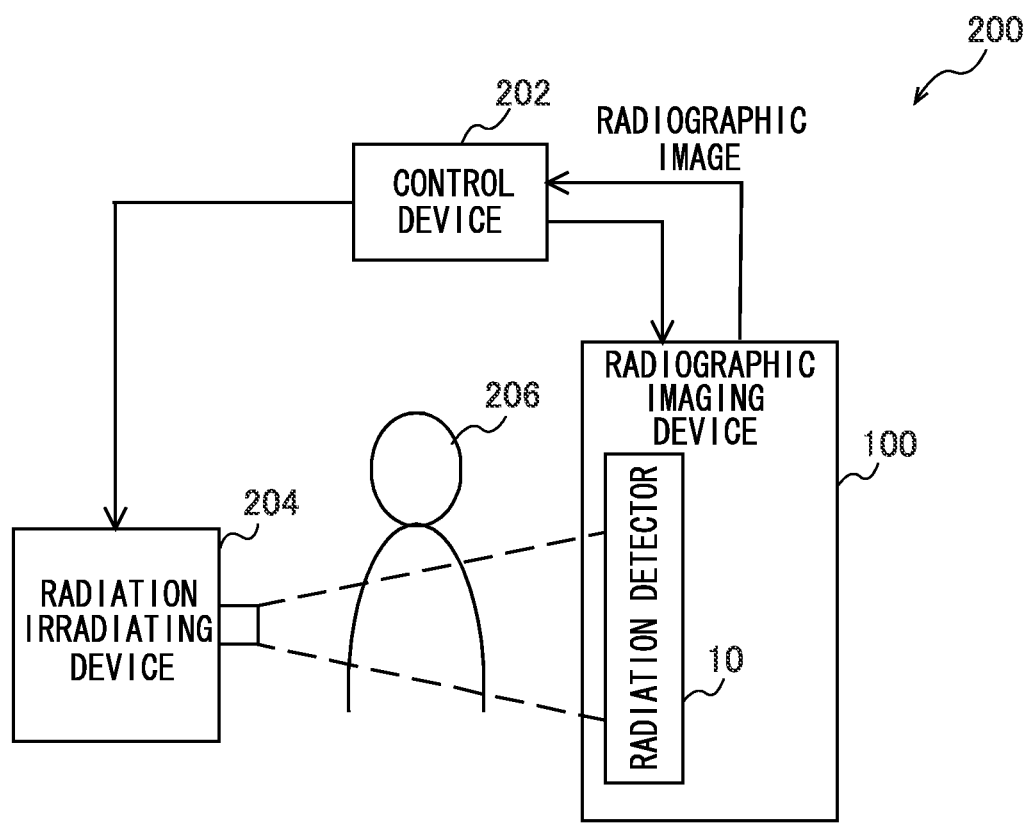
FIG. 1 is a schematic drawing showing the schematic configuration of a radiographic imaging system according to a present exemplary embodiment.

First, the schematic configuration of a radiographic imaging system that uses a radiation detector according to the present exemplary embodiment is described. FIG. 1 is a schematic drawing of an example of a radiographic imaging system of the present exemplary embodiment.

A radiographic imaging system 200 is configured to include a radiation irradiating device 204 that irradiates radiation (e.g., X-rays or the like) onto a subject 206, a radiation imaging device 100 having a radiation detector 10 that detects radiation that has been irradiated from the radiation irradiating device 204 and has passed through the subject 206, and a control device 202 that instructs imaging of radiographic images and acquires radiographic images from the radiation imaging device 100. Radiation, that has been irradiated from the radiation irradiating device 204 and that carries image information by having passed through the subject 206 who is positioned at an imaging position, is irradiated onto the radiation imaging device 100 at a timing based on control of the control device 202.

The schematic configuration of the radiation imaging device 100 of the present exemplary embodiment is described next. In the present exemplary embodiment, explanation is given of a case in which the present invention is applied to the indirect-conversion-type radiation detector 10 that converts radiation, such as X-rays or the like, into light once and converts the converted light into charges. In the present exemplary embodiment, the radiation imaging device 100 is configured to include the indirect-conversion-type radiation detector 10. Note that a scintillator that converts radiation into light is omitted from FIG. 2.

Plural pixels 20 are disposed in the form of a matrix at the radiation detector 10. The pixel 20 is configured to include a sensor portion 103 that receives light and generates charges and accumulates the generated charges, a TFT switch 4 that is a switching element for reading-out the charges accumulated in the sensor portion 103, and a radiation detection TFT switch 34 that is used in sensing according to the irradiation of radiation. In the present exemplary embodiment, the sensor portion 103 generates charges due to light, that has been converted by the scintillator, being irradiated thereon.

The plural pixels 20 are arranged in the form of a matrix in a one direction (hereinafter also called the "scan line direction") and in a direction (hereinafter also called the "signal line direction") that intersects the one direction. The array of the pixels 20 is illustrated in an abbreviated manner in FIG. 2, and, for example, 1024×1024 of the pixels 20 are arranged in the scan line direction and the signal line direction.

In the present exemplary embodiment, radiation detection pixels 20B that are used in detecting the irradiation of radiation, and other pixels 20A (mainly, pixels that are used only for detecting radiation and generating an image expressed by the radiation) are determined in advance among the plural pixels 20. Note that, hereinafter, when referring generically to the pixels 20A and the radiation detection pixels 20B without differentiating therebetween, they are simply called the pixels 20.

Figure 4:
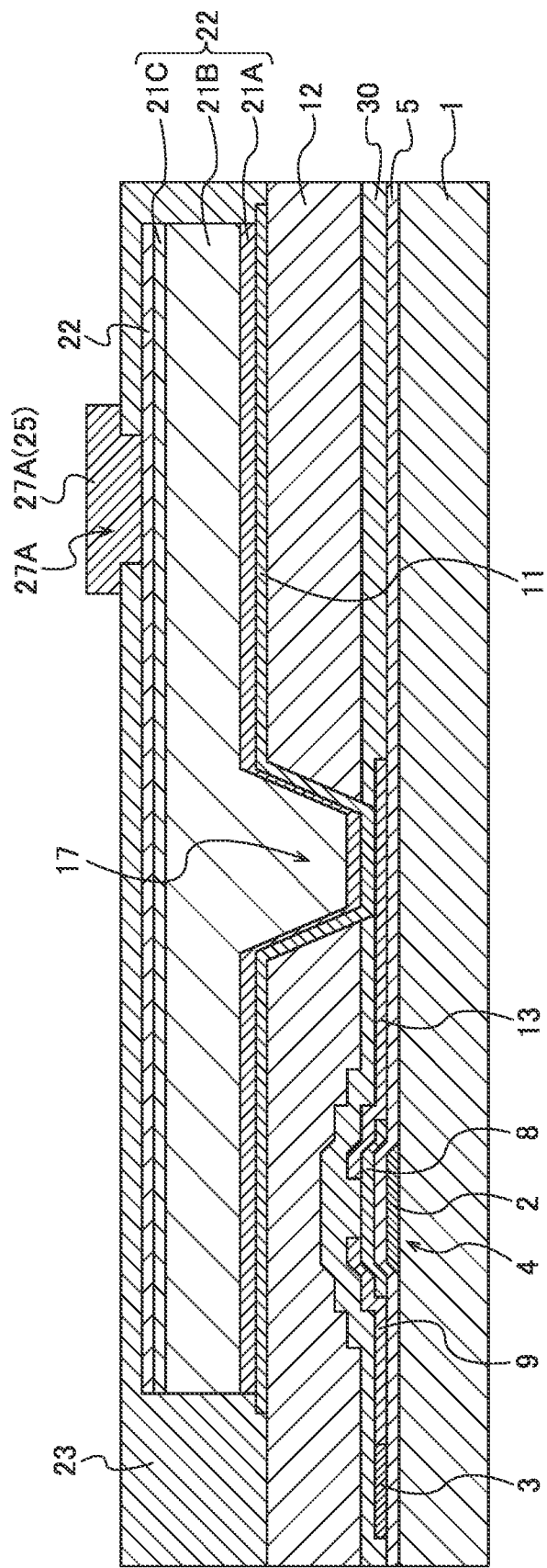
FIG. 4 is a cross-sectional view along line A-A of a pixel 20A of the radiation detector according to the present exemplary embodiment and is shown in FIG. 3.
Figure 5:
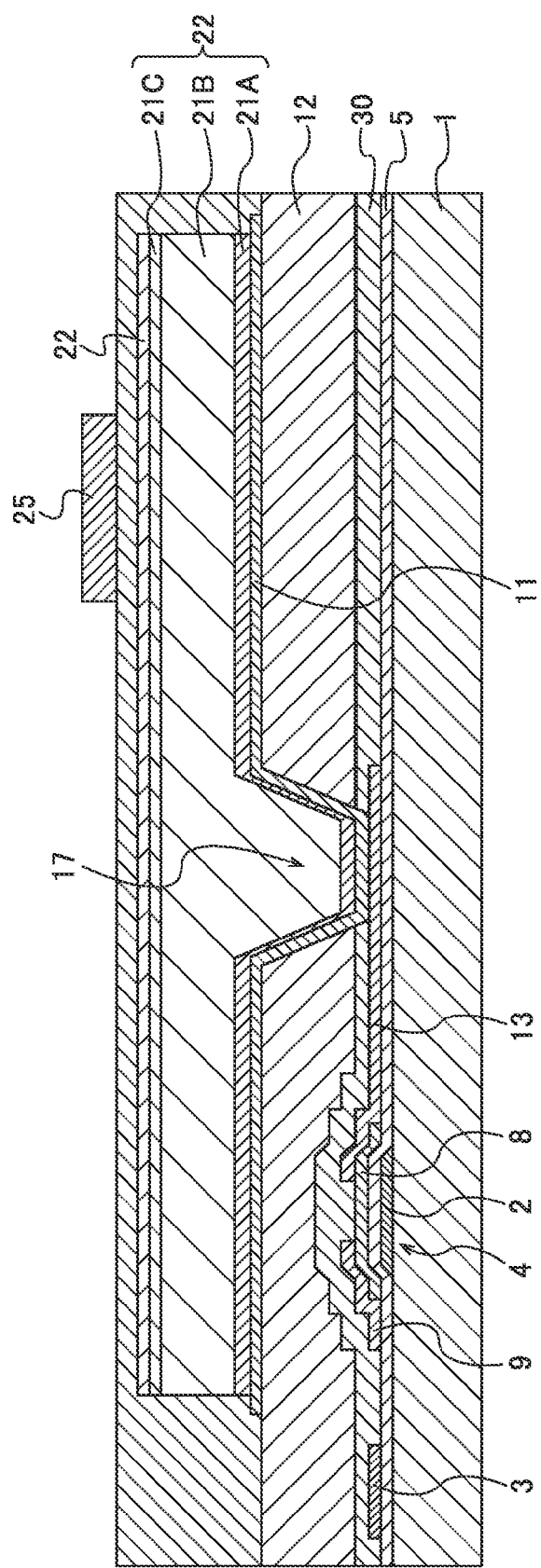
FIG. 5 is a cross-sectional view along line B-B of the pixel 20A of the radiation detector according to the present exemplary embodiment and is shown in FIG. 3.
Figure 6:
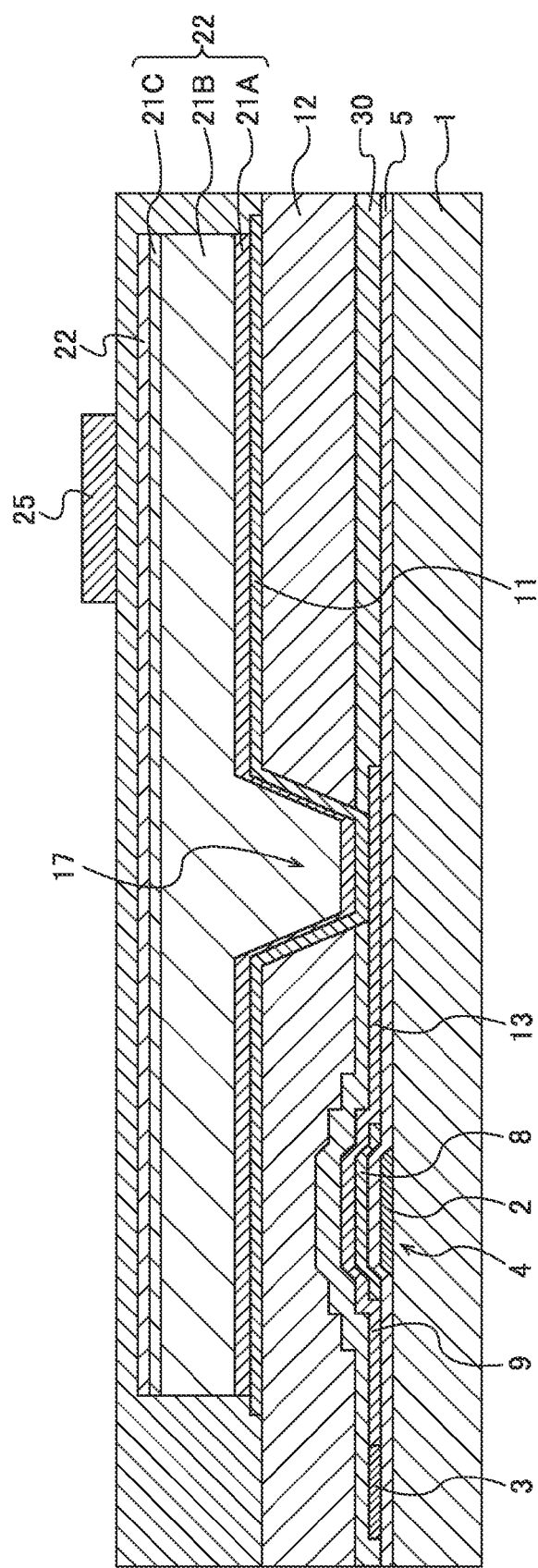
FIG. 6 is a cross-sectional view along line C-C of a radiation detection pixel 20B of the radiation detector according to the present exemplary embodiment and is shown in FIG. 3.

Plural scan lines 101, that are for turning the TFT switches 40N and OFF, and plural radiation detection scan lines 109, that are for turning the radiation detection TFT switches 34 ON and OFF, are provided in parallel on a substrate 1 (see FIG. 4 through FIG. 6). Further, on the one hand, the scan lines 101 and the radiation detection scan lines 109, and, on the other hand, plural signal lines 3 for reading-out the charges accumulated in the sensor portions 103, are provided so as to intersect one another. In the present exemplary embodiment, one of the signal lines 3 is provided for each row of pixels in one direction, and one of the scan lines 101 is provided for each row of pixels in the intersecting direction. For example, in a case in which 1024×1024 of the pixels 20 are arranged in the scan line direction and the signal line direction, there are 1024 of each of the signal lines 3 and the scan lines 101.

Figure 2:
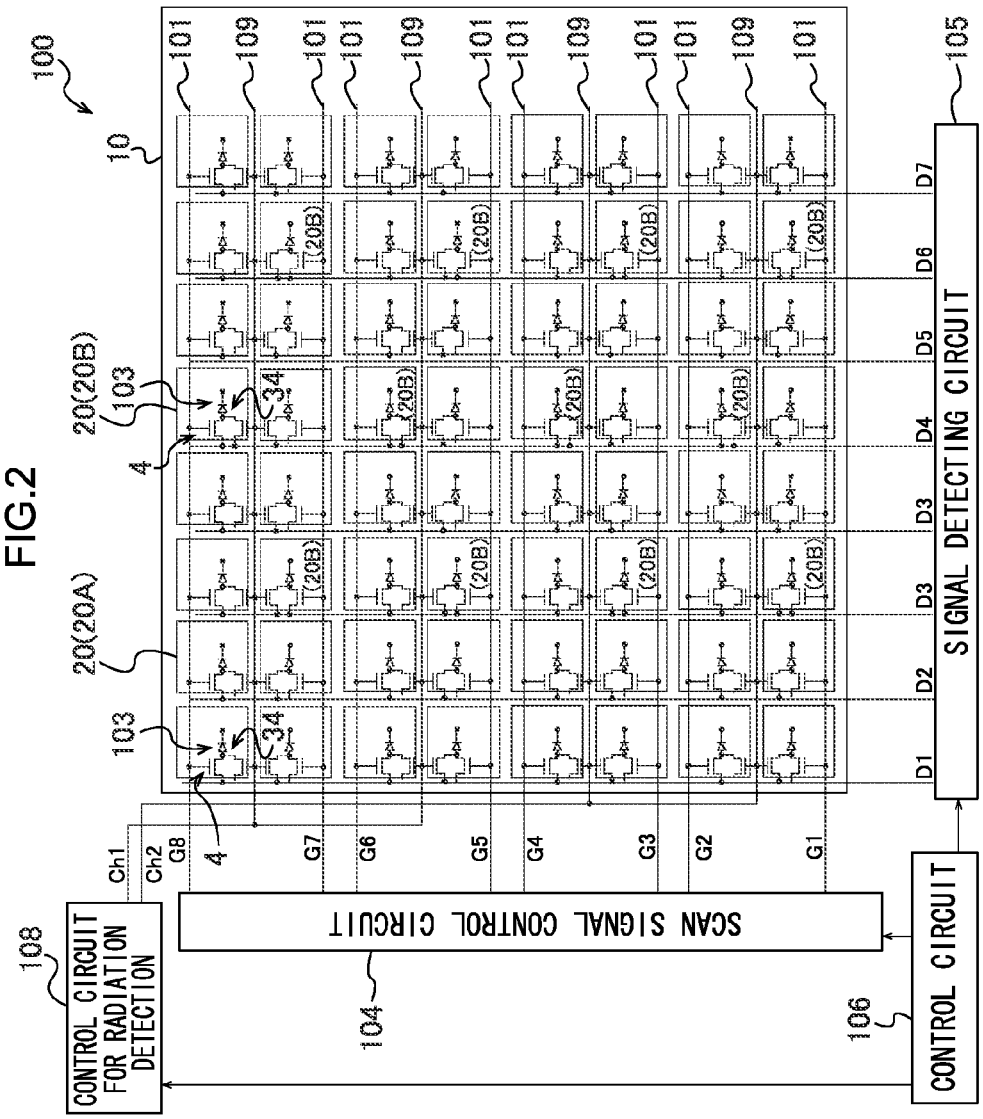
FIG. 2 is a schematic drawing showing the schematic configuration of a radiation detector according to the present exemplary embodiment.

Further, as shown in FIG. 2, the radiation detection scan line 109 are provided between the scan line 101 and the scan line 101, and the pixels 20 of adjacent rows are configured so as to have line symmetry across the radiation detection scan line 109. Therefore, in the present exemplary embodiment, for example, in a case in which 1024×1024 of the pixels 20 are arranged in the row direction and the column direction as described above, there are 1024/2=512 of the radiation detection scan lines 109.

A radiation detection control circuit 108, that outputs scan signals for turning the radiation detection TFT switches 34ON and OFF to the respective radiation detection scan lines 109, is connected to the respective radiation detection scan lines 109.

Note that, in the present exemplary embodiment, each predetermined number of the radiation detection scan lines 109 are connected collectively (connected as a single radiation detection scan line 109) to the radiation detection control circuit 108. In the case shown in FIG. 2, the radiation detection scan line 109 that is provided between scan line 101(G8) and scan line 101(G7), and the radiation detection scan line 109 that is provided between scan line 101(G6) and scan line 101(G5), are connected to the radiation detection control circuit 108 as radiation detection scan line 109(Ch1). Similarly, the radiation detection scan line 109 that is provided between scan line 101(G4) and scan line 101(G3), and the radiation detection scan line 109 that is provided between scan line 101(G2) and scan line 101(G1), are connected to the radiation detection control circuit 108 as radiation detection scan line 109(Ch2). Further, although the radiation detection pixels 20B are disposed only at one side with respect to the radiation detection scan lines 109 in FIG. 2, the radiation detection pixels 20B may be disposed at both sides with respect to the radiation detection scan lines 109. In this case, the detection sensitivity doubles.

Further, in the radiation detector 10, common electrode lines 25 are provided parallel to the respective scan lines 3. The sensor portions 103 are connected to the common electrode lines 25, and bias voltage is applied to the sensor portions 103 from a bias power source (not illustrated) via the common electrode lines 25.

Scan signals for switching the respective TFT switches 4 flow to the scan lines 101. The respective TFT switches 4 are switched due to scan signals flowing to the respective scan lines 101. Further, scan signals for switching the respective radiation detection TFT switches 34 flow to the radiation detection scan lines 109. The respective radiation detection TFT switches 34 are switched due to scan signals flowing to the respective radiation detection scan lines 109.

Electric signals, that correspond to the charges accumulated in the respective pixels 20, flow to the signal lines 3 in accordance with the switched states of the TFT switches 4 and the radiation detection TFT switches 34 of the respective pixels 20. More concretely, electric signals corresponding to the accumulated charge amounts flow to the signal line 3 due to any of the TFT switches 4 and radiation detection TFT switches 34, that are connected to that signal line 3, being turned ON.

A signal detecting circuit 105, that detects the electric signals that have flowed-out to the respective signal lines 3, is connected to the respective signal lines 3. Further, a scan signal control circuit 104, that outputs scan signals for turning the TFT switches 40N and OFF to the respective scan lines 101, is connected to the respective scan lines 101. In FIG. 2, in an abbreviated manner, one of each of the signal detecting circuit 105 and the scan signal control circuit 104 are shown. However, for example, a plurality of the signal detecting circuits 105 and a plurality of the scan signal control circuits 104 are provided, and a predetermined number (e.g., 256) of the signal lines 3 or the scan lines 101 are connected to each. For example, in a case in which 1024 of each of the signal lines 3 and the scan lines 101 are provided, four of the scan signal control circuits 104 are provided and 256 of the scan lines 101 are connected to each, and four of the signal detecting circuits 105 also are provided and 256 of the signal lines 3 are connected to each.

For each of the signal lines 3, the signal detecting circuit 105 incorporates therein an amplification circuit (see FIG. 7) that amplifies the inputted electric signal. At the signal detecting circuit 105, the electric signals inputted from the respective signal lines are amplified by the amplification circuits, and are converted into digital signals by an ADC (analog/digital converter).

A control section 106 is connected to the signal detecting circuits 105, the scan signal control circuits 104, and the radiation detection scan lines 109. The control section 106 carries out predetermined process, such as noise removal and the like, on the digital signals converted at the signal detecting circuits 105, and outputs, to the signal detecting circuits 105, control signals expressing the timing of signal detection, and outputs, to the scan signal control circuits 104, control signals expressing the timing of output of the scan signals.

The control section 106 of the present exemplary embodiment is configured by a microcomputer, and includes a CPU (central processing unit), a ROM, a RAM, and a nonvolatile storage formed by a flash memory or the like. The control section 106 carries out control for imaging radiographic images by executing, at the CPU, a program stored in the ROM.

Figure 3:
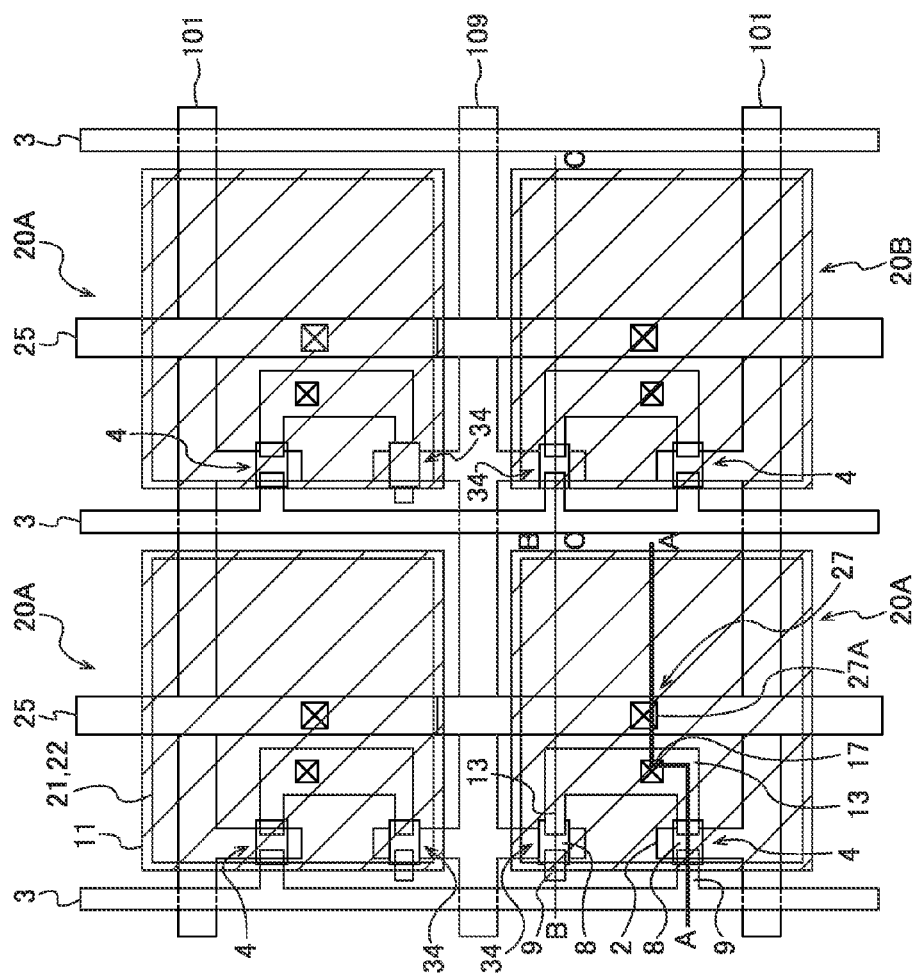
FIG. 3 is a plan view showing the configuration of the radiation detector according to the present exemplary embodiment.

A plan view showing the configuration of the indirect-conversion-type radiation detector 10 according to the present exemplary embodiment is shown in FIG. 3. A cross-sectional view along line A-A of the pixel 20A of FIG. 3 is shown in FIG. 4. A cross-sectional view along line B-B of the pixel 20A of FIG. 3 is shown in FIG. 5. A cross-sectional view along line C-C of the radiation detection pixel 20B of FIG. 3 is shown in FIG. 6.

As shown in FIG. 4 and FIG. 5, at the pixels 20A of the radiation detector 10, the scan lines 101 (see FIG. 3) and gate electrodes 2 are formed on the insulating substrate 1 that is formed from alkali-free glass or the like, and the scan lines 101 and the gate electrodes 2 are connected (see FIG. 3). The wiring layer at which the scan lines 101 and the gate electrodes 2 are formed (hereinafter, this wiring layer is also called a "first wiring layer") is formed by using Al or Cu, or a layered film formed mainly of Al or Cu. However, the material for forming the first wiring layer is not limited to these.

An insulating film 15 is formed on the entire surface on this first signal wiring layer. The region of the insulating film 15 that is positioned above the gate electrode 2 works as a gate insulating film at the TFT switch 4. The insulating film 15 is formed of, for example, $SiN_x$ or the like, and by, for example, CVD (Chemical Vapor Deposition).

Semiconductor active layers 8 are formed in shapes of islands above the gate electrodes 2 on the insulating film 15. The semiconductor active layer 8 is the channel portion of the TFT switch 4, and is formed from, for example, an amorphous silicon film.

A source electrode 9 and a drain electrode 13 are formed at the upper layer of these. Together with the source electrodes 9 and the drain electrodes 13, the signal lines 3 are formed at the wiring layer at which the source electrodes 9 and the drain electrodes 13 are formed. The source electrodes 9 are connected to the signal lines 3 (see FIG. 3). The wiring layer in which the source electrodes 9, the drain electrodes 13 and the signal lines 3 are formed (hereinafter, this wiring layer is also called a "second wiring layer") is formed by using Al or Cu, or a layered film formed mainly of Al or Cu, but is not limited to these. An impurity-added semiconductor layer (not illustrated) formed of an impurity-added amorphous silicon or the like is formed between the source electrode 9 and the drain electrode 13, and the semiconductor active layer 8. The TFT switch 4 for switching is configured by these. Note that, at the TFT switch 4, the source electrode 9 and the drain electrode 13 may be formed opposite due to the polarity of the charges that are collected and accumulated by a lower electrode 11.

Further, as shown in FIG. 5, the radiation detection TFT switch 34 is provided at the pixel 20A, in the same way as the above-described TFT switch 4. Note that, at the pixel 20A, the source electrode 9 is formed so as to not be connected to (so as to not contact) the signal line 3. Due thereto, at the pixel 20A, the charges collected at the lower electrode 11 do not flow-out to the signal line 3 via the radiation detection TFT switch 34, regardless of the switched state of the radiation detection TFT switch 34.

A TFT protective film layer 30 is formed on substantially the entire surface of the region that covers the second signal wiring layer and where the pixels 20 are provided on the substrate 1 (substantially the entire region), in order to protect the TFT switches 4 and the signal lines 3. The TFT protective film layer 30 is formed of, for example, $SiN_x$ or the like, and by, for example, CVD.

A coated interlayer insulating film 12 is formed on the TFT protective film layer 30. The interlayer insulating film 12 is formed in a film thickness of 1 μm to 4 μm by a photosensitive organic material (e.g., a positive photosensitive acrylic resin: a material in which a naphthoquinone diazide positive photosensitizer is mixed together with a base polymer including a copolymer of methacrylic acid and glycidyl methacrylate or the like) having a low permittivity (relative permittivity $\epsilon r=2$ to 4).

In the radiation detector 10 according to the present exemplary embodiment, the capacity between the metals that are disposed at the upper layer and the lower layer of the interlayer insulating film 12 is kept low by the interlayer insulating film 12. Further, generally, such a material also functions as a flattening film, and also has the effect of flattening the steps of the lower layer. In the radiation detector 10 according to the present exemplary embodiment, contact holes 17 are formed in the interlayer insulating film 12 and the TFT protective film layer 30 at positions opposing the drain electrodes 13.

The lower electrode 11 of the sensor portion 103 is formed on the interlayer insulating film 12, so as to cover the pixel region while filling-in the contact hole 17. The lower electrode 11 is connected to the drain electrode 13 of the TFT switch 4. If a semiconductor layer 21 is thick and around 1 μm, there are hardly any limitations on the material of the lower electrode 11 provided that it is electrically conductive. In such case, the lower electrode 11 may be formed by using an electrically conductive metal such as an Al-type material, ITO, or the like.

On the other hand, if the film thickness of the semiconductor layer 21 is thin (around 0.2 μm to 0.5 μm), the absorption of light at the semiconductor layer 21 may be insufficient. Therefore, in order to prevent an increase in leak current due to the illumination of light onto the TFT switch 4, it is preferable to make the semiconductor layer 21 be an alloy that is formed mainly of a light-shielding metal, or a layered film.

The semiconductor layer 21 that functions as a photodiode is formed on the lower electrode 11. In the present exemplary embodiment, a photodiode of a PIN configuration, in which an n+ layer, an i layer, and a p+ layer (n+ amorphous silicon, amorphous silicon, p+ amorphous silicon) are layered, is employed as the semiconductor layer 21, and is formed by layering an n+ layer 21A, an i layer 21B, and a p+ layer 21C in that order from the lower layer. At the i layer 21B, charges (pairs of a free electron and a free hole) are generated due to light being illuminated. The n+ layer 21A and the p+ layer 21C function as contact layers, and electrically connect the lower electrode 11 and an upper electrode 22, that is described hereinafter, with the i layer 21B.

The upper electrode 22 is formed individually on each of the semiconductor layers 21. A material having high light transmittance such as, for example, ITO or IZO (indium zinc oxide) or the like, is used as the upper electrode 22. In the radiation detector 10 according to the present exemplary embodiment, the sensor portion 103 is configured so as to include the upper electrode 22, the semiconductor layer 21, and the lower electrode 11.

A coating-type interlayer insulating film 23, that has openings 27A at portions thereof corresponding to the upper electrodes 22, is formed on the interlayer insulating film 12, the semiconductor layers 21 and the upper electrodes 22 so as to cover the respective semiconductor layers 21.

The common electrode lines 25 are formed on the interlayer insulating film 23, of Al or Cu, or an alloy or a layered film formed mainly of Al or Cu. Contact pads 27 are formed in vicinities of the openings 27A, and the common electrode lines 25 are electrically connected to the upper electrodes 22 via the openings 27A of the interlayer insulating film 23.

On the other hand, as shown in FIG. 6, at the radiation detection pixel 20B of the radiation detector 10, the radiation detection TFT switch 34 is formed such that the source electrode 9 and the signal line 3 are connected (contact one another). Due thereto, at the radiation detection pixel 20B, the charges collected by the lower electrode 11 flow-out to the signal line 3 via the radiation detection TFT switch 34, in accordance with the switched state of the radiation detection TFT switch 34.

In the radiation detector 10 that is formed in this way, as needed, a protective film is further formed from an insulating material having low light absorbance. A scintillator formed from GOS or CsI or the like is affixed to the surface thereof by using an adhesive resin having low light absorbance.

Figure 7:
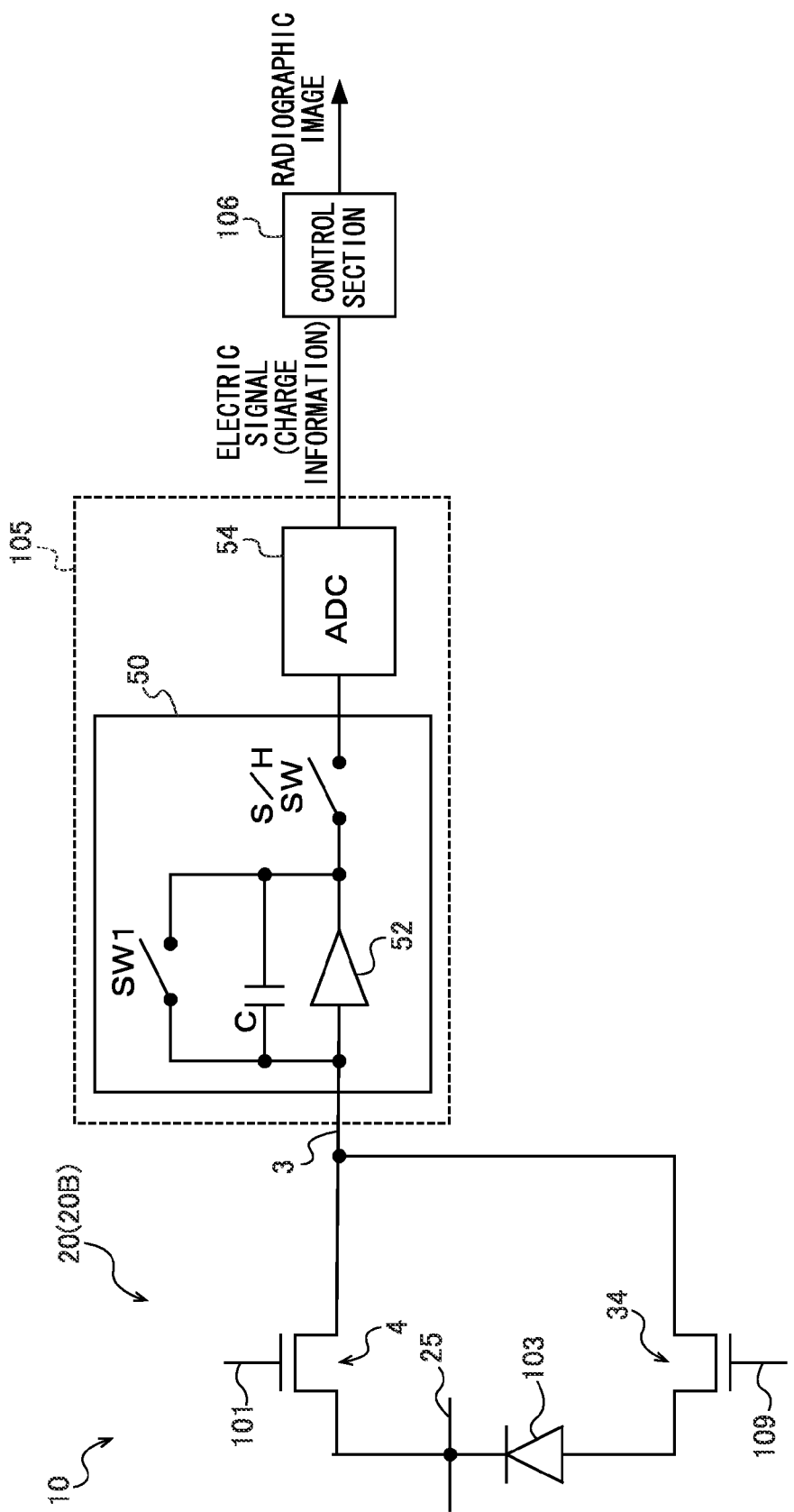
FIG. 7 is a schematic drawing showing the schematic configuration of a signal detecting circuit of the radiation detector according to the present exemplary embodiment.

The schematic configuration of the signal detecting circuit 105 of the present exemplary embodiment is described next. FIG. 7 is a schematic drawing of an example of the signal detecting circuit 105 of the present exemplary embodiment. The signal detecting circuit 105 of the present exemplary embodiment is configured to include amplification circuits 50 and an ADC (analog/digital converter) 54. Note that, although not illustrated in FIG. 7, the amplification circuit 50 is provided for each signal line 3. Namely, the signal detecting circuits 105 are configured so as to have the plural amplification circuits 50 of the same number as the number of the signal lines 3 of the radiation detector 10.

The amplification circuit 50 is configured by a charge amplification circuit, and is configured to include an amplifier 52 such as an operational amplifier or the like, a capacitor C that is connected in parallel to the amplifier 52, and a switch SW1 for charge resetting that is connected in parallel to the amplifier 52.

At the amplification circuit 50, when the switch SW1 for charge resetting is in an OFF state, charges (electric signals) are read-out from the TFT switches 4 or the radiation detection TFT switches 34 of the pixels 20, and the charges read-out from the TFT switches 4 or the radiation detection TFT switches 34 are accumulated in the capacitor C, and the voltage value outputted from the amplifier 52 is increased in accordance with the accumulated charge amount.

Further, the control section 106 applies a charge resetting signal to the switch SW1 for charge resetting, and controls the ON/OFF state of the switch SW1 for charge resetting. Note that, when the switch SW1 for charge resetting is set in an on state, the input side and the output side of the amplifier 52 are short-circuited, and the charges of the capacitor C are discharged.

The ADC 54 has the function of, when an S/H (sample-and-hold) switch SW is in an ON state, converting the electric signal, that is the analog signal inputted from the amplification circuit 50, into a digital signal. The ADC 54 successively outputs the electric signals, that have been converted into digital signals, to the control section 106.

Note that the electric signals, that are outputted from all of the amplification circuits 50 provided at the signal detecting circuit 105, are inputted to the ADC 54 of the present exemplary embodiment. Namely, the signal detecting circuit 105 of the present exemplary embodiment has the one ADC 54 regardless of the number of amplification circuits 50 (signal lines 3).

In the present exemplary embodiment, the electric signals of the signal lines 3, to which the radiation detection TFT switches 34 of the radiation detection pixels 20B are connected (in FIG. 2, the signal lines D3, D4, D5), are detected at the amplification circuits 50 of the signal detecting circuit 105. The control section 106 compares the values of the digital signals converted by the signal detecting circuit 105 with a predetermined threshold value for radiation detection, and carries out detection according to the irradiation of radiation, such as detecting whether or not radiation has been irradiated or the like, in accordance with whether or not the values of the digital signals are greater than or equal to the threshold value. This is a so-called synchronization-free configuration in which control signals from the control device 202 are not needed. Note that the detection, by the control section 106, of whether or not radiation has been irradiated is not limited to comparison with a threshold value for radiation detection. For example, detection may be carried out on the basis of a condition that is set in advance, such as the number of times of sensing, or the like.

Note that the "detection" of an electric signal in the present exemplary embodiment means the sampling of the electric signal.

Figure 8:
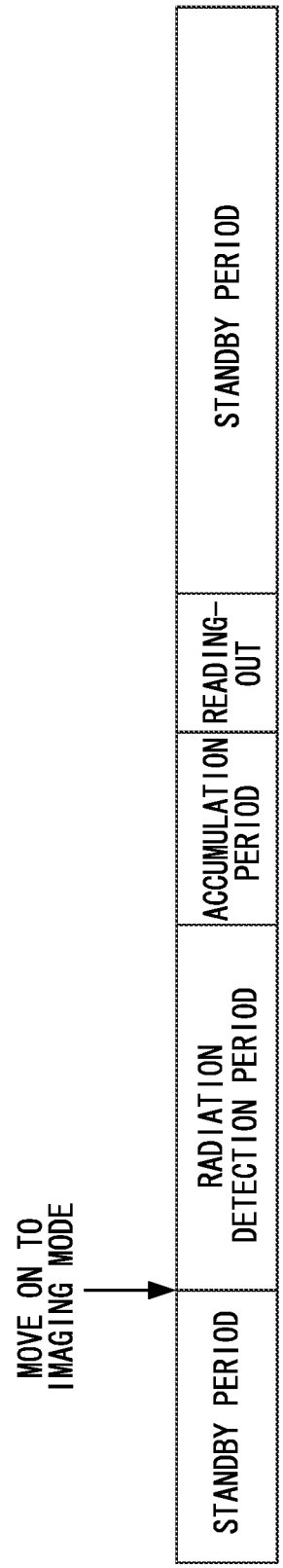
FIG. 8 is a schematic drawing that schematically shows the flow of operations at the time of imaging a radiographic image, of a radiographic imaging device according to the present exemplary embodiment.

Next, the flow of operations at the time of imaging a radiographic image by the radiation imaging device 100 of the above-described configuration is described simply by using FIG. 8.

At the radiation detector 10 of the present exemplary embodiment, even in a state in which radiation is not being irradiated, charges are generated due to dark current or the like, and the charges are accumulated in the respective pixels 20. Therefore, in the radiographic imaging device 100, a resetting operation, in which the charges accumulated in the respective pixels 20 of the radiation detector 10 are removed and eliminated, is carried out repeatedly also during the standby state. The information expressed by the charges that are read-out in this resetting operation is utilized in correcting noise (offset) that arises in the radiographic image due to dark current or the like. Further, in the present exemplary embodiment, the state in which the power of the radiation detector 10 (the radiographic imaging device 100) is OFF is a standby period.

The radiographic imaging device 100 captures a radiographic image by detecting the start of irradiation of radiation and starts the accumulation of charges at the respective pixels 20 of the radiation detector 10. At the time when imaging of a radiographic image is carried out, the control device 202 notifies the radiographic imaging device 100 of the move to an imaging mode.

When the radiographic imaging device 100 is notified of the move to the imaging mode, the radiographic imaging device 100 moves on to a radiation detection period in which detection of the start of irradiation of radiation is carried out (this is a standby state for the irradiation of radiation). When the start of irradiation of radiation is detected, the radiographic imaging device 100 moves on to an accumulation period in which charges are accumulated in the respective pixels 20 of the radiation detector 10. A predetermined time after the detecting of the start of irradiation of radiation, or when the completion of the accumulation period is detected, the radiographic imaging device 100 moves on to a read-out state in which the accumulated charges are read-out, and, after the reading-out of the charges ends, again moves on to the standby state. Note that offset information may be continued to be acquired after the end of the reading-out of the charges.

Figure 9:
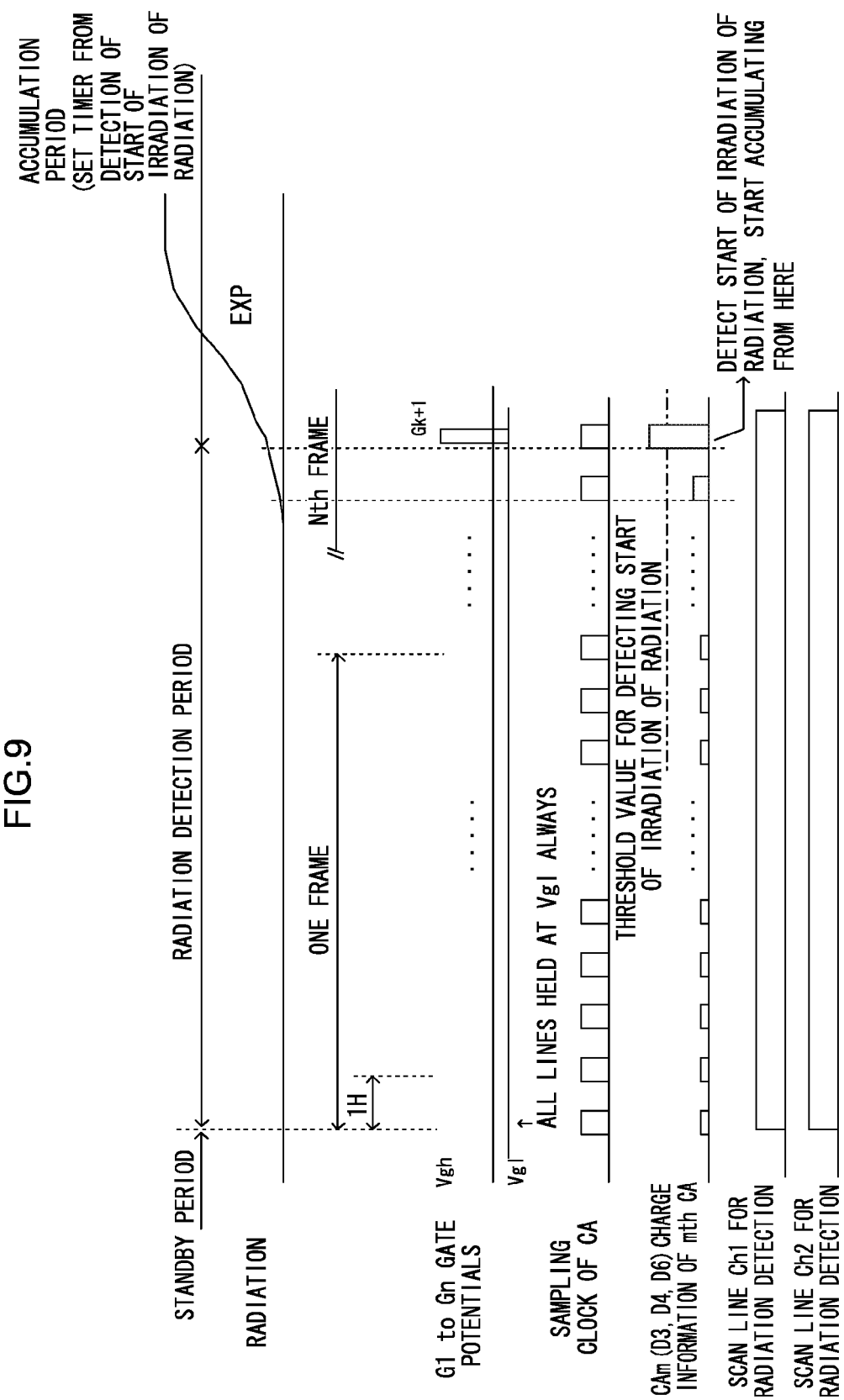
FIG. 9 is a time chart showing in detail the flow of operations at the time of imaging a radiographic image, of the radiographic imaging device according to the present exemplary embodiment.

Next, the flow of operations at the time of imaging a radiographic image by the radiation imaging device 100 according to the present exemplary embodiment is described in detail. A time chart, that shows in detail the flow of operations of the radiographic imaging device 100 according to the present exemplary embodiment at the time of imaging a radiographic image, is shown in FIG. 9. Note that FIG. 9 is a time chart that shows in detail operations during a radiation detection period that is after the aforementioned standby period has ended, and the radiographic imaging device 100 has moved on to the imaging mode.

In the radiographic imaging device 100 of the present exemplary embodiment, during the radiation detection period, the scan signal control circuit 104 is controlled, and scan signals of gate potential Vg1 are outputted from the scan signal control circuits 104 to the respective scan lines 101 (G1 through Gn). Due thereto, the TFT switches 4 of the respective pixels 20 are maintained in OFF states.

On the other hand, the radiation detection control circuit 108 is controlled, and scan signals of gate potential Vgh are outputted from the control circuit 108 to the respective radiation detection scan lines 109 (Ch1, Ch2). Due thereto, during the radiation detection period, the radiation detection TFT switches 34 of the respective pixels 20 are maintained in ON states. At this time, at the pixels 20A, the radiation detection TFT switches 34 are not connected to the signal lines 3, and therefore are in ON states, but charges are not outputted to the signal lines 3 via the radiation detection TFT switches 34. On the other hand, at the radiation detection pixels 20B, the radiation detection TFT switches 34 are connected to the signal lines 3, and therefore, charges are outputted to the signal lines 3 via the radiation detection TFT switches 34, in accordance with their being in ON states. Further, in the present exemplary embodiment, the electric signals that flow to the signal lines 3 are converted into digital data and sampling thereof is repeated by the amplification circuits (CA: charge amplifiers) 50 of the signal detecting circuit 105 at a predetermined cycle 1H.

The control section 106 compares the digital data values, that were converted by the signal detecting circuit 105, of the signal lines 3 to which the radiation detection pixels 20B are connected, with a predetermined threshold value for detecting the start of irradiation of radiation, and, in accordance with whether or not this threshold value is exceeded, carries out detection of whether or not the irradiation of radiation has started. If the threshold value is exceeded, the control section 106 detects that the irradiation of radiation has started, and the radiographic imaging device 100 moves on to the aforementioned accumulation period.

In the accumulation period, scan signals of the gate potential Vg1 are outputted from the radiation detection control circuit 108 to the respective radiation detection scan lines 109 (Ch1, Ch2). Due thereto, the radiation detection TFT switches 34 of the respective pixels 20 are maintained in OFF states. Due to the radiation detection TFT switches 34 being set in OFF states, at the radiation detection pixels 20B as well, the charges of the sensor portions 103 can be accumulated during the accumulation period. Accordingly, a radiographic image may be generated by using the charges outputted from the radiation detection pixels 20B (the electric signals corresponding to the charges).

Note that the flow of operations at the time of imaging a radiographic image by the radiographic imaging device 100 according to the present exemplary embodiment is not limited to the above. Another example is described with reference to FIG. 10. Note that, similarly to above-described FIG. 9, FIG. 10 as well is a time chart that shows in detail operations during a radiation detection period that is after the aforementioned standby period has ended, and the radiographic imaging device 100 has moved on to the imaging mode.

Figure 10:
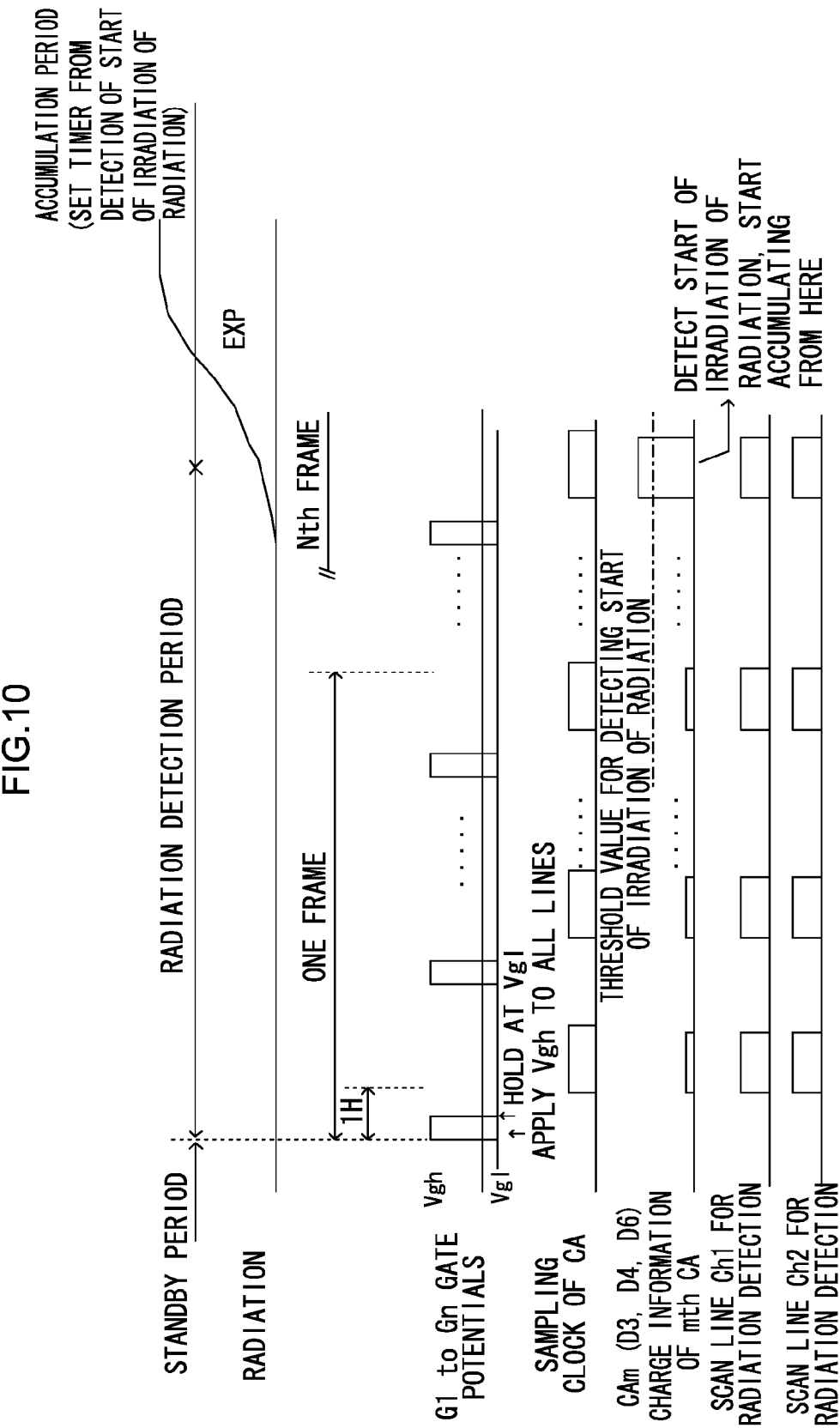
FIG. 10 is a time chart showing in detail another example of the flow of operations at the time of imaging a radiographic image, of the radiographic imaging device according to the present exemplary embodiment.

In the case shown in FIG. 10, during the radiation detection period, the scan signal control circuit 104 is controlled, and scan signals of the gate potential Vgh are outputted repeatedly at the predetermined cycle 1H that is a resetting cycle, from the scan signal control circuit 104 to the respective scan lines 101 (G1 through Gn). Due thereto, the TFT switches 4 of the respective pixels 20 enter into ON states, and the resetting operation, that removes the charges accumulated in the respective pixels 20, is executed repeatedly at the resetting cycle 1H.

On the other hand, while scan signals of the gate potential Vgh for the resetting operation are being outputted to the respective scan lines 101 as described above, scan signals of the gate potential Vg1 are outputted from the radiation detection control circuit 108 to the respective radiation detection scan lines 109 (Ch1, Ch2). Due thereto, during the resetting operation, the radiation detection TFT switches 34 of the respective pixels 20 enter into OFF states. Thereafter, when the scan signals flowing to the respective scan lines 101 become the gate potential Vg1 and the TFT switches 4 enter into OFF states, scan signals of the gate potential Vgh are outputted from the radiation detection control circuit 108 to the radiation detection scan lines 109, and the radiation detection TFT switches 34 of the respective pixels 20 enter into ON states. In the same way as described above, in accordance with the radiation detection TFT switches 34 entering into ON states, the electric signals that flow to the signal lines 3 are converted into digital data, and sampling thereof is repeated by the amplification circuits (CA: charge amplifiers) 50 of the signal detecting circuit 105. Moreover, as described above, the control section 106 compares the digital data values of the signal lines 3 to which the radiation detection pixels 20B are connected, which digital data values were converted by the signal detecting circuit 105, and the predetermined threshold value for detecting the start of irradiation of radiation. When the threshold value is exceeded, it is detected that irradiation of radiation has started, and the radiographic imaging device 100 moves on to the accumulation period. Still further, in this case as well, during the accumulation period, due to scan signals of the gate potential Vg1 being outputted from the radiation detection control circuit 108 to the respective radiation detection scan lines 109 (Ch, Ch2), charges can be accumulated in the sensor portions 103 during the accumulation period at the radiation detection pixels 20B as well. Accordingly, a radiographic image may be generated by also the using the charges outputted from the radiation detection pixels 20B (the electric signals corresponding to the charges).

Note that, in the above explanation, the start of irradiation of radiation is detected by, for each of the signal lines 3, sampling the electric signal, and comparing the electric signal with the threshold value for detecting the start of irradiation of radiation. However, the start of irradiation of radiation may be detected at each block that is formed from a predetermined number of the pixels 20. An example of a case of carrying out detection per block is shown in FIG. 11 and FIG. 12.

Figure 11:
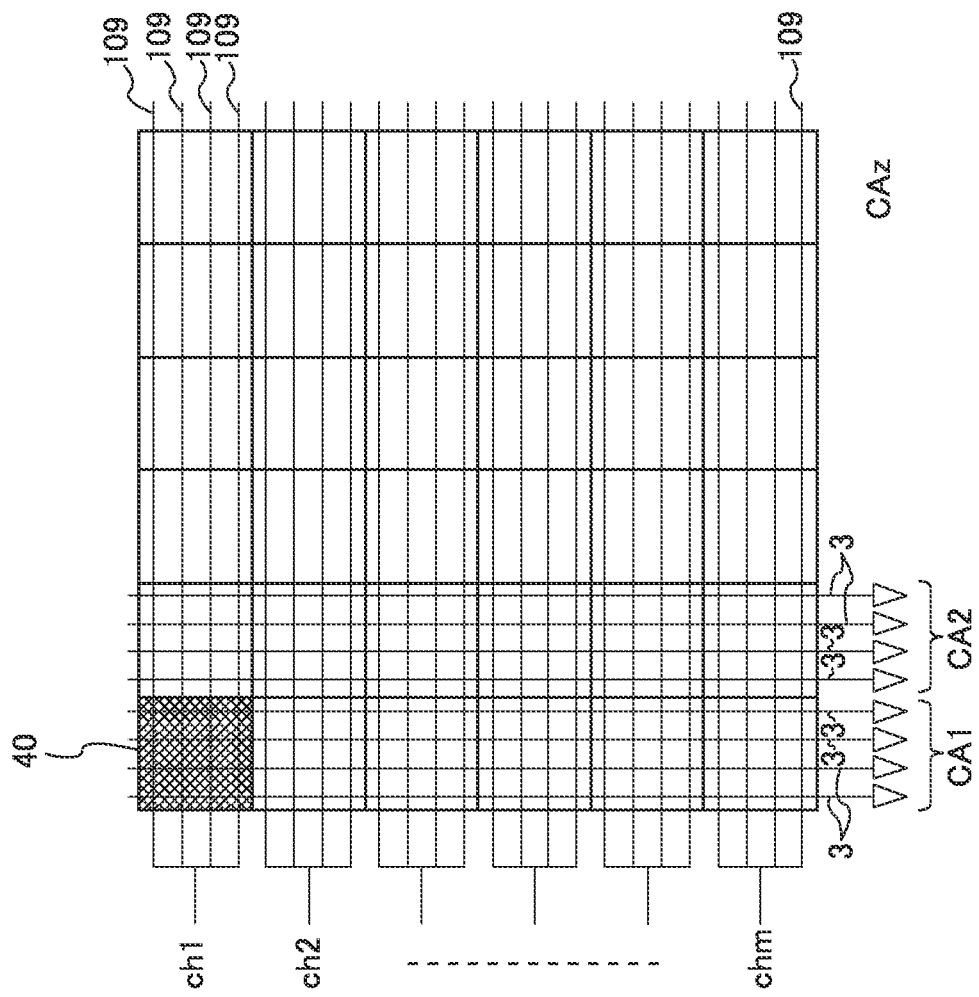
FIG. 11 is an explanatory drawing for explaining a case of carrying out detection according to the irradiation of radiation per block, in the radiographic imaging device according to the present exemplary embodiment.
Figure 12:
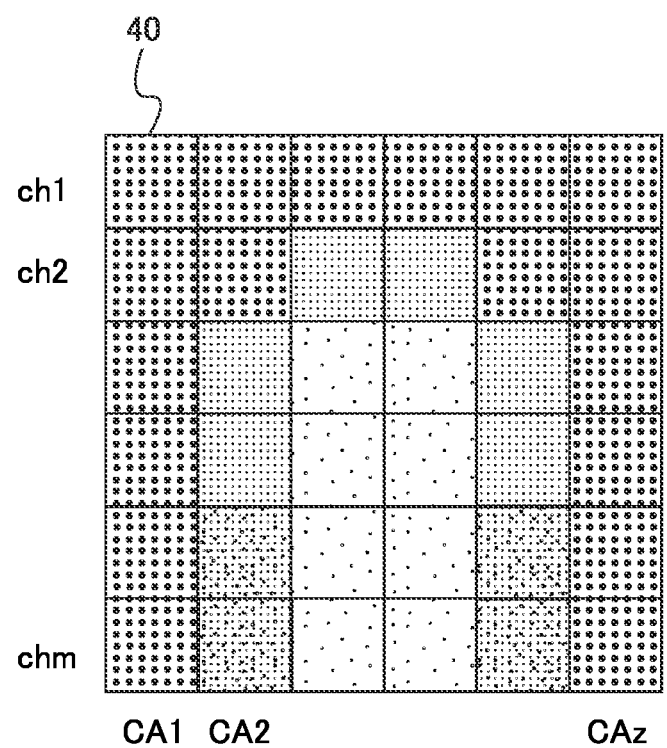
FIG. 12 is an explanatory drawing for explaining a case of carrying out detection according to the irradiation of radiation per block, in the radiographic imaging device according to the present exemplary embodiment.

FIG. 11 illustrates a case in which four (four rows) of the radiation detection scan lines 109 are connected, as a single radiation detection scan line 109 (Ch), to the radiation detection control circuit 108. One block 40 is the pixels 20 that are configured by the one radiation detection scan line 109 (Ch) and four (four columns) of the signal lines 3. Concretely, in the case of the radiographic imaging device 100 (the radiation detector 10) shown in FIG. 2, the one block 40 is formed by 32 of the pixels 20, which are the pixels 20 of eight rows×the pixels 20 of four columns=32 of the pixels 20.

When detecting the start of irradiation of radiation, scan signals, that are such that the radiation detection TFT switches 34 are turned ON, are outputted successively from the radiation detection control circuit 108 to the radiation detection scan lines 109 (Ch1 through Chm). In the signal detecting circuit 105, the average charge amount, that is generated in accordance with the irradiated radiation, is acquired per block 40 as shown in FIG. 12, by reading the average charge amounts (the electric signals corresponding to the average charge amounts) of the signal lines 3, to which the radiation detection pixels 20B are connected, by time division at the amplification circuits 50 per block 40 (CA1 through CAz). Note that FIG. 12 shows that, the higher the density of the block 40, the greater the average charge amount, and accordingly, the greater the dose of the irradiated radiation.

For each block 40, the control section 106 compares the digital data value of the average charge amount that was read with a threshold value for detecting the start of irradiation of radiation. In a case in which the threshold value is exceeded, the start of irradiation of radiation is detected.

As described above, the radiation detector 10 of the radiographic imaging device 100 of the present exemplary embodiment has: the pixels 20A that have the sensor portion 103 that generates charges in accordance with light that has been converted from irradiated radiation, the TFT switch 4 that outputs, to the signal line 3, the charges read-out from the sensor portion 103, and the radiation detection TFT switch 34 that is not connected to the signal line 3; and the radiation detection pixels 20B that have the sensor portion 103, the TFT switch 4, and the radiation detection TFT switch 34 that is connected to the signal line 3 and outputs, to the signal line 3, the charges read-out from the sensor portion 103. The control terminal of the radiation detection TFT switch 34 is connected to the radiation detection scan line 109, and the on/off state is controlled by scan signals outputted from the radiation detection control circuit 108.

In this way, in the radiation detector 10 of the present exemplary embodiment, during the accumulation period and the read-out period, OFF signals flow from the radiation detection control circuit 108 to the radiation detection scan lines 109, and, due thereto, the radiation detection TFT switches 34 can be set in OFF states. Due thereto, an increase in the wiring capacity of the signal lines 3, that is due to the radiation detection pixels 20B being connected, may be prevented. Of the parasitic capacity that arises at the radiation detector 10, the parasitic capacity that is due to the pixel capacity of the pixels 20 is subjective. For example, in a case in which the parasitic capacity per pixel 20 is around 2 pF and 100 of the radiation detection pixels 20B are connected, the parasitic capacity increases as much as 200 pf. On the other hand, because the signal line capacity of the signal line 3 is around 200 pF, by providing the radiation detection pixels 20B, the wiring capacity (parasitic capacity) doubles. In the present exemplary embodiment, by setting the radiation detection TFT switches 34 in OFF states as described above, an increase in parasitic capacity due to the radiation detection pixels 20B may be prevented.

The difference in the wiring capacities of the signal lines 3, to which the radiation detection pixels 20B are connected, and the signal lines 3, to which only the pixels 20A are connected and the radiation detection pixels 20B are not connected, may be prevented from becoming large. Accordingly, detection according to the irradiation of radiation may be carried out while maintaining the quality of the radiographic image as is.

Further, in the present exemplary embodiment, the radiation detection pixels 20B also are configured so as to have the TFT switch 4. Because a radiographic image can be generated by using the charge information (electric signals) read-out from the radiation detection pixels 20B, the radiation detection pixels 20B becoming point defects may be suppressed, and the quality of the generated radiographic image may be maintained.

Further, in the present exemplary embodiment, by providing the radiation detection scan line 109 between two of the scan lines 101, there is a so-called mirror-reversed pixel pattern in which the pixels 20A and the radiation detection pixels 20B have line symmetry across the radiation detection scan line 109. Due to such a configuration, as compared with a case in which the wire of the radiation detection scan line 109 is provided for each row of pixels 20, the number of wires of the radiation detection scan lines 109 may be halved, and an increase in noise due to the increase in the radiation detection scan lines 109 may be suppressed, the quality of the radiographic image may be maintained, and a decrease in yield may be suppressed.

Further, in the present exemplary embodiment, during the radiation detection period, scan signals, that set in the radiation detection TFT switches 34 in ON states, are outputted to the radiation detection scan lines 109, and the start of irradiation of radiation may be detected while successively resetting the pixels 20. By doing so, artifacts caused by the reset cycle changing may be prevented, and therefore, the quality of the radiographic image may be maintained.

Further, in the present exemplary embodiment, due to the configuration in which the radiation detection TFT switches 34 are provided at the pixels 20A as well, the pixels 20A and the radiation detection pixels 20B can be made to have substantially the same configurations. Generally, when inspecting the radiation detector 10 by an inspection device, the radiation detection pixels 20B being detected as defective (errors), due to the difference between the shape (pattern) of the pixels 20A and the shape of the radiation detection pixels 20B, can be prevented. Accordingly, limitations on an inspection device (e.g., an optical inspection device) may be avoided. Further, for example, if the shape (pattern) of the pixel 20A and the shape (pattern) of the radiation detection pixels 20B differ greatly, a repeating pattern of a mask that is used in manufacturing the radiation detector 10 may not be used, and therefore, there are cases in which manufacturing is difficult. However, because manufacturing can be carried out by using a repeating pattern of a mask, the radiation detector 10 may be made easy to manufacture.

Figure 13:
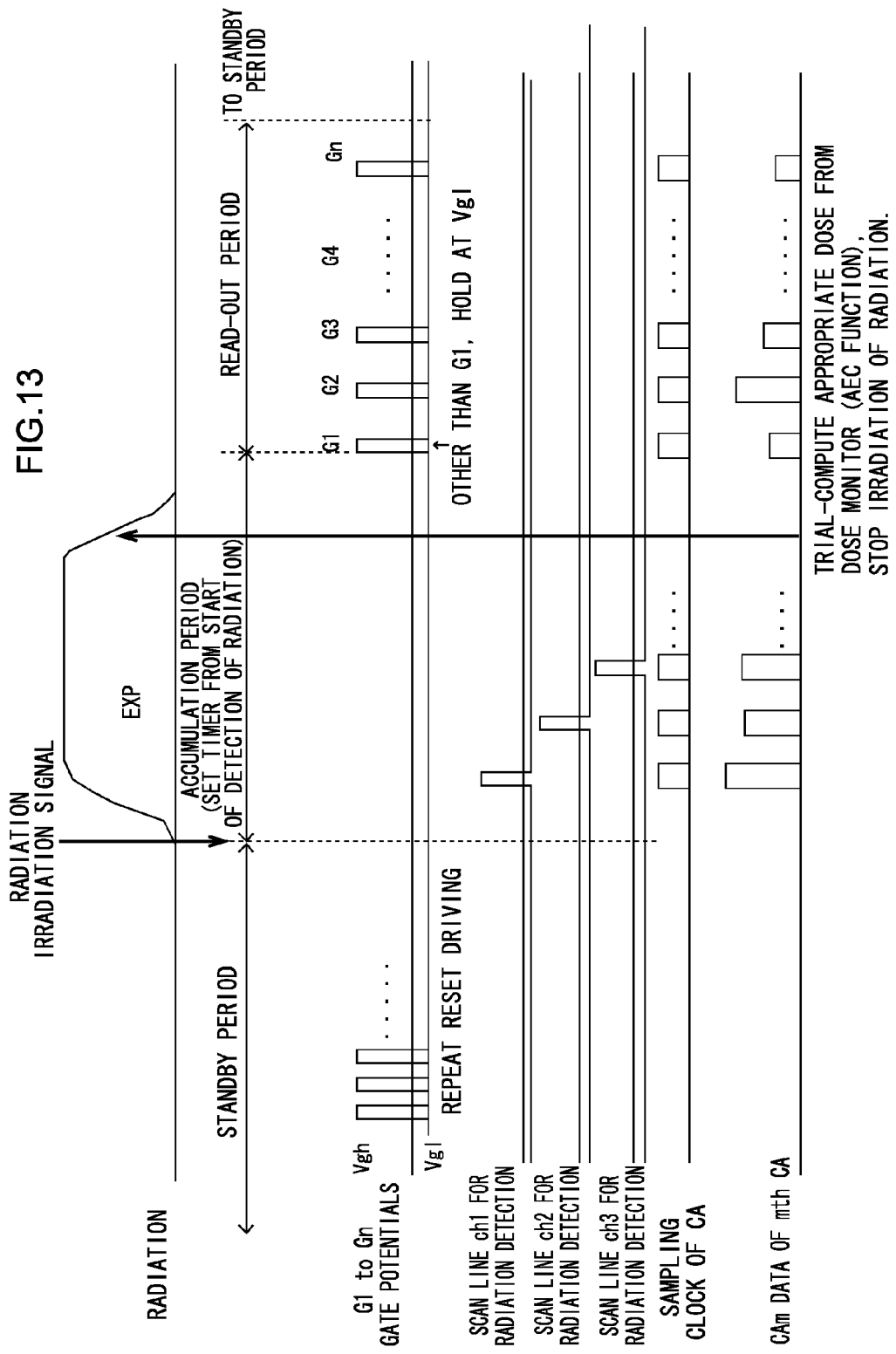
FIG. 13 is a time chart showing in detail the flow of operations at the time of detection (AEC) according to the irradiation of radiation, of the radiographic imaging device according to the present exemplary embodiment.

Note that, in the present exemplary embodiment, a case in which the start of irradiation of radiation is detected, have been described. However, the present invention is not limited thereto, and may carry out other detection according to the irradiation of radiation. For example, the present invention may be utilized in controlling the irradiation of radiation, in a case in which there is synchronization with the control device 202 of the radiation in FIG. 1. As shown in FIG. 13, sampling, in which electric signals, that flow to the signal lines 3 to which the radiation detection pixels 20B are connected, are converted into digital data by the signal detecting circuit 105 and detection of radiation is carried out, is repeated at the predetermined cycle 1H also during the accumulation period after detection of the start of irradiation of radiation, and the values of the digital data of the signal lines 3 to which the radiation detection pixels 20B are connected are compared with a predetermined threshold value for radiation detection, and the irradiation of radiation is stopped when the cumulative amount exceeds the threshold value, or, the time when the cumulative amount will exceed the threshold value is predicted and the irradiation of radiation is stopped at this time when exceeding of the threshold value is predicted. Further, similarly, the present invention may also be applied to real time gain switching, such as achieving the optimal gain that corresponds to the dose. In a configuration in which the capacity of the capacitor C of the amplifier 52 that is a charge amplifier can be changed to several levels (C1, C2, C3 . . . ) in the signal detecting circuit 105 such as shown in FIG. 7, in a case in which it is determined, from the value of the digital data of the signal line 3 to which the radiation detection pixel 20B is connected, that the dose is low, the capacity of the capacitor is changed and the amplification factor of the amplifier is raised such that the S/N ratio becomes higher, and, in a case in which it is determined that the dose is high, the amplification factor of the amplifier is lowered and the amplification factor of the signals from the pixels 20A that are read-out thereafter is changed so as to become optimal so that the signals are not saturated.

Further, in the radiation detector 10 (see FIG. 2) of the radiation imaging device 100 of the present exemplary embodiment, the radiation detection pixels 20B are connected to some of the signal lines 3. However, the present invention is not limited thereto, and the radiation detection pixels 20B may be provided at positions connected to all of the signal lines 3.

Further, in the present exemplary embodiment, a case in which one of the radiation detection scan lines 109 is provided per two of the scan lines 101 (so as to correspond to two rows of the pixels 20), have been described. However, the present invention is not limited thereto, and may be configured such that one of the radiation detection scan lines 109 is provided per another number of the scan lines 101 (per pixels 20 of another number of rows). Further, in the present exemplary embodiment, each two of the radiation detection scan lines 109 (corresponding to four rows of the pixels 20) are connected as one radiation detection scan line 109 (Ch) to the radiation detection control circuit 108. However, the present invention is not limited thereto, and each of another number of the radiation detection scan lines 109 (corresponding to another number of rows of the pixels 20) may be connected as one radiation detection scan line 109 (Ch) to the radiation detection control circuit 108.

Figure 14:
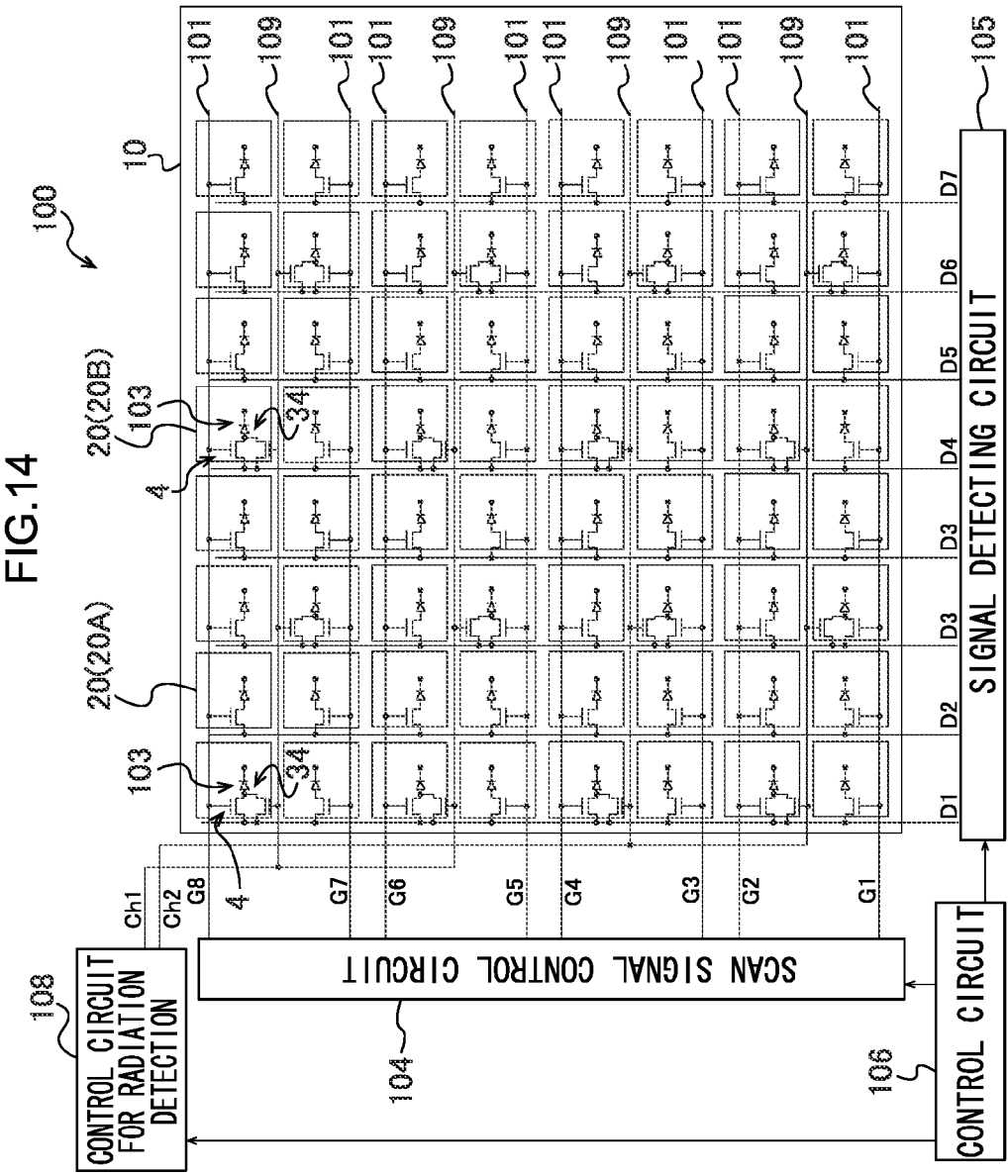
FIG. 14 is a drawing showing another example of the overall configuration of the radiation detector according to the present exemplary embodiment.

Further, in the present exemplary embodiment, a case in which the pixels 20A of the radiation detector 10 also have the radiation detection TFT switches 34, have been described. However, as shown in FIG. 14, the pixels 20A may be configured so as to not have the radiation detection TFT switches 34. Also in the radiation detector 10 of the present exemplary embodiment that is shown in FIG. 2, the radiation detection TFT switches 34 of the pixels 20A are not connected to the signal lines 3, and charges are not read-out via the radiation detection TFT switches 34. Therefore, in a case in which the radiation detection TFT switches 34 are not provided at the pixels 20A as shown in FIG. 14, detection according to the irradiation of radiation may be carried out appropriately.

Further, in the present exemplary embodiment, a case in which an indirect-conversion type radiation detector 10 that generates charges in accordance with light obtained by irradiated radiation being converted by a scintillator, have been described. However, the present invention is not limited thereto, and may be applied to a direct-conversion type that directly converts radiation into charges at a semiconductor layer and accumulates the charges. In this case, the sensor portions in a direct-conversion type generate charges due to radiation being irradiated thereon.

In addition, the configurations, operations and the like of the radiation imaging device 100, the radiation detector 10, the pixels 20 and the like that were described in the present exemplary embodiment are examples, and may, of course, be changed in accordance with the situation within a range that does not deviate from the gist of the present invention.

Further, in the present exemplary embodiment, the radiation of the present invention is not particularly limited, and X-rays, γ-rays or the like can be used.

What is claimed is:

1. A radiation detector comprising:
   a plurality of signal lines,
   a plurality of first pixels including,
      a first sensor portion that generates charges in accordance with irradiated radiation, and
      a first switching element that reads-out the charges generated at the first sensor portion and outputs the charges to a signal line;
   a plurality of second pixels including,
      a second sensor portion that generates charges in accordance with irradiated radiation,
      a second switching element that reads-out the charges generated at the second sensor portion and outputs the charges to a signal line, and
      a radiation detection switching element that reads-out the charges generated at the second sensor portion and outputs the charges to the signal line to which the charges read-out by the second switching element flow;
   a plurality of scan lines that are formed from at least one of
      a scan line group formed from scan lines to which control terminals of the first switching elements are connected and through which control signals that switch the first switching elements flow, and scan lines to which control terminals of the second switching elements are connected and through which control signals that switch the second switching elements flow, or a scan line group to which the control terminals of the first switching elements and the control terminals of the second switching elements are connected and through which control signals that switch the first switching elements and the second switching elements flow; and
   a plurality of radiation detection scan lines that are provided between predetermined scan lines among the plurality of scan lines, and to which control terminals of the radiation detection switching elements are connected, and through which radiation detection control signals that switch the radiation detection switching elements flow,
   wherein the plurality of signal lines are formed from
      either a signal line group formed from signal lines to which the charges output from the first pixels and the charges output from the second pixels flow,
      or a signal line group formed from
         signal lines to which the charges output from the first pixels and the charges output from the second pixels flow and
         signal lines to which the charges output from the first pixels flow.

2. The radiation detector of claim 1, wherein each of the first pixels includes the radiation detection switching element whose control terminal is connected to the radiation detection scan line, that is not connected to a signal line.

3. The radiation detector of claim 2, wherein the first pixels and the second pixels are configured to have shapes that are line-symmetrical across the radiation detection scan lines.

4. A radiographic imaging device comprising:
   the radiation detector of claim 3;
   a radiation detection control circuit that outputs the radiation detection control signals to the radiation detection switching elements of the radiation detector; and
   detecting section that carry out predetermined detection according to irradiation of radiation, on the basis of electric signals corresponding to the charges that are outputted to the signal lines from the radiation detection switching elements of the second pixels.

5. The radiation detector of claim 2, wherein the plurality of radiation detection scan lines are connected, per each predetermined number thereof, to a radiation detection control circuit from which the radiation detection control signals are outputted.

6. A radiographic imaging device comprising:
the radiation detector of claim 2;
a radiation detection control circuit that outputs the radiation detection control signals to the radiation detection switching elements of the radiation detector; and
detecting section that carry out predetermined detection according to irradiation of radiation, on the basis of electric signals corresponding to the charges that are outputted to the signal lines from the radiation detection switching elements of the second pixels.

7. The radiation detector of claim 1, wherein the first pixels and the second pixels are configured to have shapes that are line-symmetrical across the radiation detection scan lines.

8. The radiation detector of claim 7, wherein the plurality of radiation detection scan lines are connected, per each predetermined number thereof, to a radiation detection control circuit from which the radiation detection control signals are outputted.

9. A radiographic imaging device comprising:
the radiation detector of claim 7;
a radiation detection control circuit that outputs the radiation detection control signals to the radiation detection switching elements of the radiation detector; and
detecting section that carry out predetermined detection according to irradiation of radiation, on the basis of electric signals corresponding to the charges that are outputted to the signal lines from the radiation detection switching elements of the second pixels.

10. The radiation detector of claim 1, wherein the plurality of radiation detection scan lines are connected, per each predetermined number thereof, to a radiation detection control circuit from which the radiation detection control signals are outputted.

11. A radiographic imaging device comprising:
the radiation detector of claim 1;
a radiation detection control circuit that outputs the radiation detection control signals to the radiation detection switching elements of the radiation detector; and
detecting section that carry out predetermined detection according to irradiation of radiation, on the basis of electric signals corresponding to the charges that are outputted to the signal lines from the radiation detection switching elements of the second pixels.

12. The radiographic imaging device of claim 11, wherein, during a detection period in which a start of irradiation of radiation is detected by the detecting section, control signals that set the first switching elements and the second switching elements in OFF states flow to the scan lines, and the radiation detection control signals that set the radiation detection switching elements in ON states flow to the radiation detection scan lines.

13. The radiographic imaging device of claim 12, wherein, during a detection period in which a start of irradiation of radiation is detected by the detecting section, a resetting operation, that resets charges accumulated in the first pixels and the second pixels is repeated at a predetermined cycle, by flowing control signals that set the first switching elements and the second switching elements in ON states to the scan lines.

14. The radiographic imaging device of claim 12, wherein, when the first switching elements and the second switching elements are set in ON states and the charges for imaging radiographic image are outputted from the first pixels and the second pixels to the signal lines, the radiation detection switching elements are set in OFF states.

15. The radiographic imaging device of claim 11, wherein, during a detection period in which a start of irradiation of radiation is detected by the detecting section, a resetting operation, that resets charges accumulated in the first pixels and the second pixels is repeated at a predetermined cycle, by flowing control signals that set the first switching elements and the second switching elements in ON states to the scan lines.

16. The radiographic imaging device of claim 15, wherein, when the first switching elements and the second switching elements are set in ON states and the charges for imaging radiographic image are outputted from the first pixels and the second pixels to the signal lines, the radiation detection switching elements are set in OFF states.

17. The radiographic imaging device of claim 11, wherein, when the first switching elements and the second switching elements are set in ON states and the charges for imaging radiographic image are outputted from the first pixels and the second pixels to the signal lines, the radiation detection switching elements are set in OFF states.

18. A radiographic imaging system comprising:
an irradiation device that irradiates radiation; and
the radiographic imaging device of claim 11 that detects the radiation irradiated from the irradiation device and acquires a radiographic image corresponding to detected radiation.

* * * * *